US00PP19820P3

(12) United States Plant Patent
Worley

(10) Patent No.: US PP19,820 P3
(45) Date of Patent: Mar. 10, 2009

(54) ***SALVIA* PLANT NAMED 'DANCING DOLLS'**

(50) Latin Name: *Salvia hybrida*
Varietal Denomination: Dancing Dolls

(75) Inventor: Patrick J. Worley, Watsonville, CA (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 11/882,873

(22) Filed: Aug. 6, 2007

(65) Prior Publication Data

US 2009/0044305 P1 Feb. 12, 2009

(51) Int. Cl.
*A01H 5/00* (2006.01)

(52) U.S. Cl. ..... Plt./475

(58) Field of Classification Search ..... Plt./475
See application file for complete search history.

*Primary Examiner*—Annette H Para
*Assistant Examiner*—June Hwu
(74) *Attorney, Agent, or Firm*—Buchanan Ingersoll & Rooney PC

(57) ABSTRACT

A new and distinct *Salvia hybrida* plant is provided that is the product of a controlled breeding program. Over an extended period of time attractive large bi-colored blossoms are formed that are rose and cream in coloration. The plant is vigorous and quick growing, and asexually reproduces well through the use of cuttings. The growth habit is compact and somewhat upright. Good disease resistance has been observed during observations to date. The plant is well suited for providing attractive ornamentation.

2 Drawing Sheets

Botanical/commercial classification: *Salvia hybrida/ Salvia* Plant.
Varietal denomination: cv. Dancing Dolls.

SUMMARY OF THE INVENTION

The new cultivar of *Salvia* plant of the present invention was created during 2003 at Watsonville, Calif., U.S.A., by artificial pollination wherein two parents were crossed which previously had been studied in the hope they would contribute the desired characteristics. The female parent (i.e., the seed parent) was an unnamed and non-patented *Salvia microphylla* plant, and the male parent (i.e., the pollen parent) was an unnamed and non-patented *Salvia muelleri* plant. The parentage of the new cultivar can be summarized as follows:

*Salvia microphylla*×*Salvia muelleri.*

The seeds resulting from the above pollination were sown and small plants were obtained which physically and biologically different from each other. Selective study resulted in the identification of a single plant of the new cultivar.

It was found that the new *Salvia* cultivar possesses the following combination of characteristics:

(a) displays a vigorous quickly growing, compact, and somewhat upright growth habit, (b) displays over an extended period of time attractive large bi-colored blossoms that are rose and cream in coloration, (c) displays good disease resistance, and (d) is well suited for providing attractive ornamentation.

The new cultivar can be readily distinguished from its ancestors in view of its more compact growth habit and distinctive ornamental bi-colored blossom coloration.

The new cultivar of the present invention can be readily distinguished from *Salvia macrophylla* 'Hot Lips' (non-patented in the United States) and *Salvia muelleri.* Both the new variety of the present invention and the 'Hot Lips' variety bear bi-colored blossoms; however, those of the 'Hot Lips' variety are red and white in coloration while those of the new variety are rose and cream in coloration. The blossoms of *Salvia muelleri* are of a dissimilar rich purple coloration.

The new cultivar well meets the needs of the horticultural industry and can be grown to advantage as attractive ornamentation in parks, gardens, public areas, and residential landscapes.

The new cultivar has been asexually reproduced by the rooting of cuttings for several generations. Such asexual reproduction as performed at Watsonville, Calif., U.S.A., and West Grove, Pa., U.S.A., has demonstrated that the characteristics of the new cultivar are firmly fixed and stable and are strictly transmissible from one generation to another. The new cultivar asexually reproduces in a true-to-type manner from one generation to another.

The new cultivar has been named 'Dancing Dolls'.

BRIEF DESCRIPTION OF THE PHOTOGRAPHS

The accompanying photographs show as nearly true as it is reasonably possible to make the same, in color illustrations of this character, typical specimens of the new cultivar while growing outdoors. In each instance the plants had been reproduced by the use of cuttings in greenhouses and subsequently had been transplanted to the outdoors. The plants were less than one year in age.

DETAILED DESCRIPTION

Figure 1:
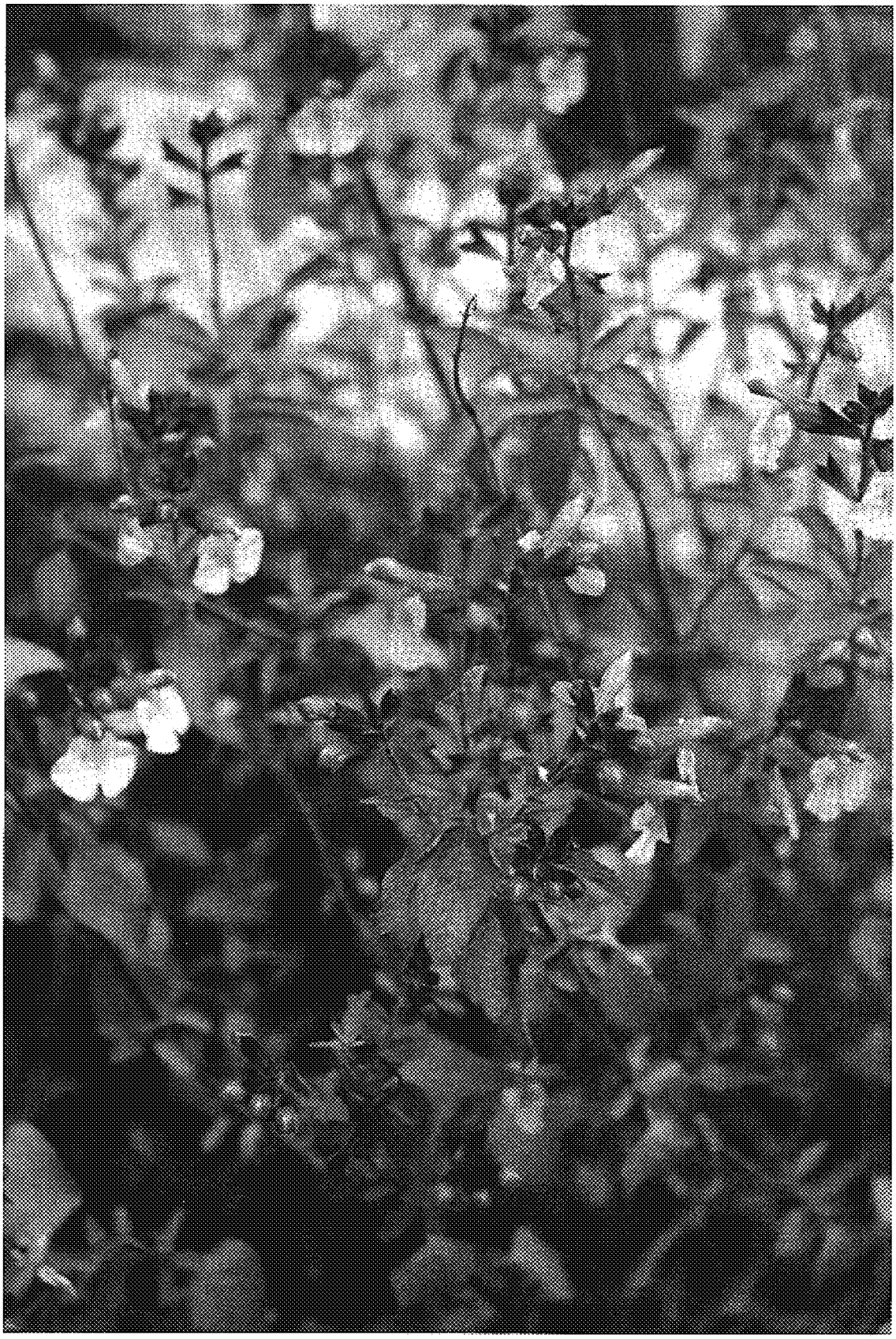
FIG. 1 illustrates a close view of the attractive blossoms and foliage of the new cultivar on Jul. 3, 2007 while being grown at West Grove, Pa., U.S.A.
Figure 2:
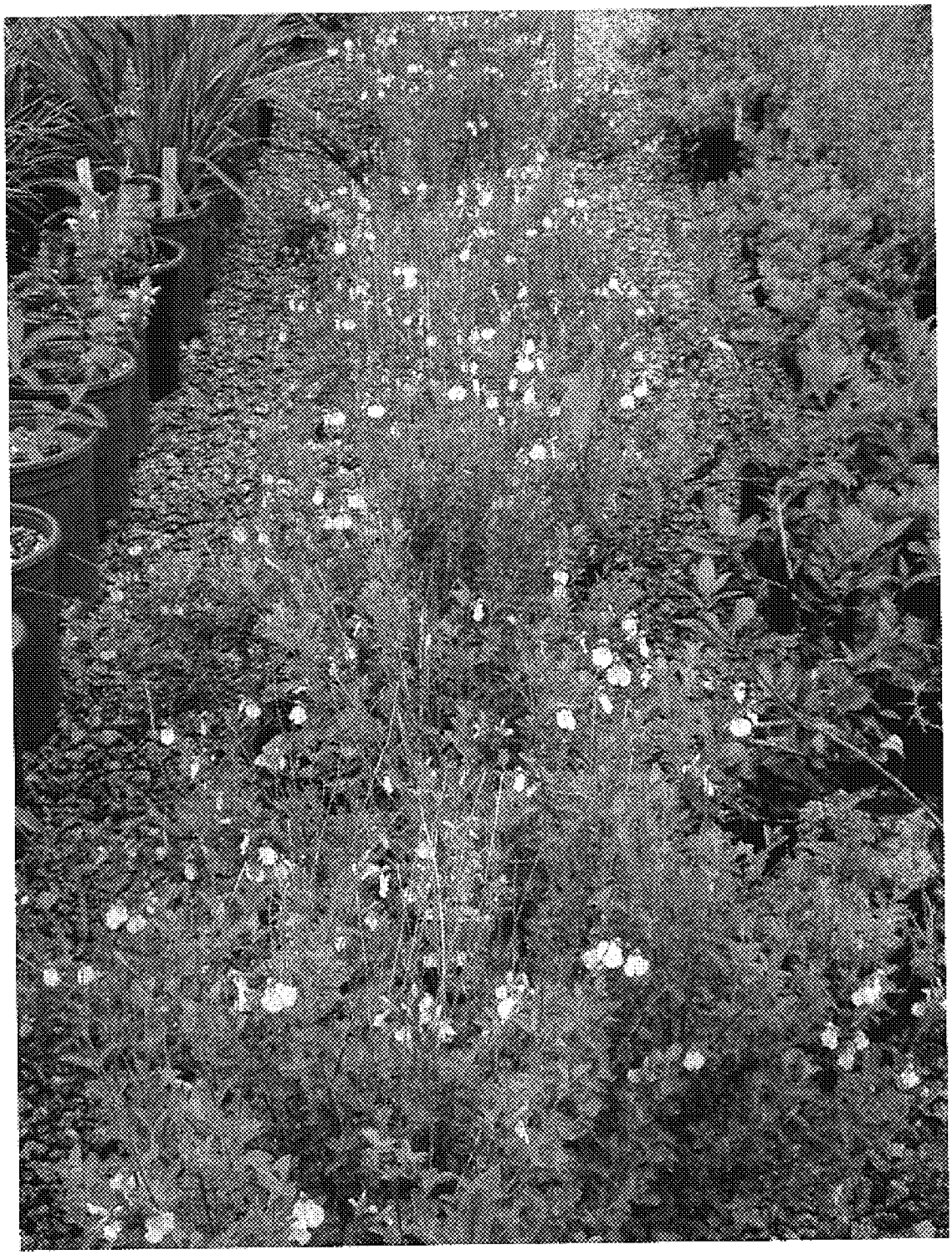
FIG. 2 illustrates a mass planting in a row of the new cultivar when flowering during early June, 2007, while being grown at Watsonville, Pa., U.S.A.

The chart used in the identification of colors is that of The Royal Horticultural Society (R.H.S. Colour Chart) of London, England. Color terminology in common terms sometimes is included as an aid to the reader. Such color terminology is to be accorded its customary dictionary significance. The description is based on the observation of typical specimens of the new cultivar during June while growing outdoors at West Grove, Pa., U.S.A.

Plant:

*Form.*—Bushy, vigorous quickly growing, compact, and somewhat upright.

Height.—Commonly up to approximately 1 meter.

*Width.*—Commonly approximately 0.7 m.

*Growth habit.*—Perennial.

*Leaf arrangement.*—Opposite.

*Leaf configuration.*—Elliptic to oblong.

*Leaf length.*—Commonly variable from approximately 1.2 to 3 cm.

*Leaf width.*—Commonly variable from approximately 0.7 to 2.5 cm.

*Leaf margin.*—Crenulate.

*Leaf texture.*—Commonly slightly fleshy, glandular on the upper surface, and rough on the under surface.

*Leaf venation.*—Prominently visible and branched.

*Leaf blade color.*—Yellow-Green Group 144A on the upper surface, and near Yellow-Green Group 138B on the under surface.

*Leaf blade apex.*—Acute to obtusely rounded.

*Leaf blade base.*—Primarily attenuate.

*Petiole length.*—Variable and commonly approximately 3 to 10 mm.

*Petiole width.*—Commonly approximately 1 to 1.5 mm.

*Petiole color.*—Yellow-Green Group 145B.

Inflorescence:

*Time.*—Typically initiates blooming near mid-May.

*Type.*—Terminal raceme.

*Diameter.*—Commonly approximately 2 cm at the widest point.

*Length.*—Commonly approximately 10 to 12 cm.

*Number.*—Commonly up to approximately 12 decussate pairs.

*Configuration.*—Tubular, and two-lipped.

*Peduncle length.*—Commonly approximately 3 mm.

*Peduncle color.*—Near Violet-Blue Group 93B.

*Peduncle texture.*—Smooth and puberulent.

*Pedicel length.*—Commonly approximately 3 to 6 mm.

*Pedicel width.*—Commonly approximately 0.5 to 0.8 mm.

*Pedicel texture.*—Glandular and puberulent.

*Pedicel color.*—Purplish, near Purple Group 79B.

*Calyx shape.*—Broadly campanulate and flared towards the apex.

*Calyx rib number.*—Commonly 10 and longitudinally disposed.

*Calyx length.*—Commonly approximately 10 mm on average.

*Calyx width.*—Commonly up to 6 mm.

*Calyx texture.*—Glandular and puberulent on the upper and under surfaces.

*Calyx color.*—On the upper lobe and the lower lobes primarily Purple Group 79B at the apex and changing to Yellow-Green Group 144C at the base.

*Calyx lobe number.*—3.

*Calyx upper lobe number.*—1.

*Calyx upper lobe shape.*—Acute.

*Calyx upper lobe length.*—Commonly approximately 4 mm on average.

*Calyx upper lobe width.*—Commonly approximately 4 mm in width.

*Calyx lower lobe number.*—2.

*Calyx lower lobe shape.*—Acute.

*Calyx lower lobe length.*—Commonly approximately 3 mm on average.

*Calyx lower lobe width.*—Commonly approximately 4 mm on average.

*Corolla shape.*—Tubular proximally to two-lipped distally.

*Corolla length.*—Commonly approximately 2.2 to 2.5 cm on average.

*Corolla color.*—The base commonly is near Yellow-White Group 158C, the tube is near Red-Purple Group 64B, and the lower lip is near Red Group 38D.

*Corolla tube length.*—Approximately 17 mm on average.

*Corolla tube width.*—Approximately 3 mm on average.

*Corolla tube depth.*—Approximately 8 mm on average.

*Corolla tube lip number.*—2.

*Corolla upper lip number.*—1.

*Corolla upper lip shape.*—Hood-like.

*Corolla upper lip length.*—Commonly approximately 11 mm average.

*Corolla lower lip length.*— 2, suborbicular.

*Corolla lower lip shape.*—Banner-like, and extended downward.

*Corolla lower lip outline.*—Obovate.

*Corolla lower lip length.*—Commonly approximately 20 mm on average.

*Corolla lower lip diameter at tip.*—Approximately 12 mm on average.

*Style length.*—Approximately 2.5 to 3 cm on average.

*Style width.*—Commonly near 1 mm on average.

*Style texture.*—Pubescent towards the tip.

*Style attachment site.*—At four-lobed ovary between lobes.

*Stamen number.*—2.

*Stamen shape.*—Seesaw-like.

*Filament length.*—Approximately 5 mm on average.

*Connective length.*—Approximately 14 mm on average.

*Anther attachment site.*—At outer end of the connective.

Development:

*Vegetation.*—Vigorous quickly growing, and compact.

*Blooming.*—Long blooming season commonly extending for approximately 20 weeks.

*Fertility.*—Not observed to date.

*Winter hardiness.*—A full hardiness evaluation has not been conducted to date; however, the new cultivar has been shown to be hardy to at least U.S.D.A. Hardiness Zone No. 7.

*Disease resistance.*—Very good during observations to date, and displays resistance to stem root, root rot, powdery mildew, and Botrytis.

I claim:

1. A new and distinct *Salvia* plant characterized by the following combination of characteristics:

(a) displays a vigorous quickly growing, compact, and somewhat upright growth habit, (b) displays over an extended period of time attractive large bi-colored blossoms that are rose and cream in coloration, (c) displays good disease resistance, and, (d) is well suited for providing attractive ornamentation; substantially as illustrated and described.

* * * * *